United States Patent [19]

Leonardi

[11] Patent Number: 4,677,974
[45] Date of Patent: Jul. 7, 1987

[54] METHOD AND APPARATUS FOR IMMOBILIZING AN EYELID

[76] Inventor: David Leonardi, 2320 Plaza del Grande, Las Vegas, Nev. 89102

[21] Appl. No.: 781,457

[22] Filed: Sep. 30, 1985

[51] Int. Cl.⁴ .............................................. A61F 13/12
[52] U.S. Cl. .................................... 128/163; 128/76.5
[58] Field of Search ...................... 128/163, 76.5, 380; 604/308; 2/15

[56] References Cited

U.S. PATENT DOCUMENTS

| | | | |
|---|---|---|---|
| 1,161,321 | 11/1915 | Lush | 604/308 |
| 2,365,032 | 12/1944 | Wilkenson | 128/163 |
| 2,543,104 | 2/1951 | Golding | 128/163 |
| 3,339,206 | 9/1967 | Daley | 128/163 |
| 3,952,735 | 4/1976 | Wirtschafter et al. | 128/163 |
| 4,303,063 | 12/1981 | Stahl | 128/163 |
| 4,411,263 | 10/1983 | Cook | 2/15 |
| 4,473,370 | 9/1984 | Weiss | 128/163 |

*Primary Examiner*—Edgar S. Burr
*Assistant Examiner*—Tonya Lamb
*Attorney, Agent, or Firm*—Seiler, Quirk & Tratos

[57] ABSTRACT

An eyelid splint is provided for comfortably immobilizing the lid of an injured or diseased eye. The splint consists of a soft, resilient pad, preferably of synthetic foam having a thickness of at least 7 mm, having a backing which is attached to two elastic straps. The straps have adjustable interengaging fasteners to permit adjustment of the pressure on the eyelid to be between 23 and 40 mm Hg.

8 Claims, 6 Drawing Figures

METHOD AND APPARATUS FOR IMMOBILIZING AN EYELID

BACKGROUND OF THE INVENTION

This invention relates to a method of immobilizing an eyelid of an injured eye by means of an eyelid splint. More particularly, it relates to a thick, resilient, foam pad which may be mounted on a head-encircling device for compressing the eyelid, thereby rendering it immobile.

Physicians frequently encounter situations in which a patient's eyelid requires immobilization. Typical examples in which the eyelid must be maintained in a fixed, closed position to permit healing include corneal abrasions, corneal ulcers, corneal burns, keratitis (corneal inflammation) resulting from chemical insults, ultraviolet light, or drying (keratitis sicca), or following corneal surgery, e.g., pteryguim removal, repair of corneal lacerations, or for certain post-operative complications following corneal or cataract surgery. Eyelid immobilization is also helpful to prevent injuries to the cornea from drying when a patient is unable to close the eyelid due to neurologic deficiencies caused by e.g., Bell's palsy, stroke, head injury, or coma.

At present, eyelid immobilization is effected by taping a cotton pad over the closed eyelid, with the tape extending across the patient's face. Various thicknesses of cotton and amounts of tape are used depending on the underlying condition. Frequently, tincture of benzoin, a flammable adhesive solution, is used to augment the adhesiveness of the tape. The principle of eyelid immobilization in the event of eye injury or disease is similar to the purpose of casting or splinting broken bones. By rendering the bones immobile, they are given time to heal. By rendering an eyelid immobile, the cornea is permitted to heal, and the risk of additional injury during the healing period is minimized.

The current invention comprises an eyelid splint which is mounted on the head of the patient by a pair of head-encircling straps. The straps are elastic, and their length is adjustable, in order to adjust the pressure of the splint against the eyelid. The pad is fabricated from a thick, resilient foam which, upon compression, assumes the shape of the eye socket, thereby preventing the lid from moving. Pressure is adjustable through the adjustment of the straps, optimally to a level of not less than 23 mm Hg and not more than 40 mm Hg. The appliance of the invention has proven significantly superior to prior art methods of eyelid immobilization for a number of reasons. Firstly, the current taped-pad state-of-the-art for splinting eyelids is quite uncomfortable. Patients often complain of more pain after splinting than before, because a large amount of tape must be stretched tightly across facial skin to immobilize the lid. Frequently, tincture of benzoin must be used to ensure adhesion for the necessary 12 to 24 hours of required immobilization. The tape is uncomfortable, pulling on facial skin. Because of the discomfort inflicted by the patch, patients may require narcotics in order to sleep, and frequently will remove the patches on their own prior to the actual healing of the eye, leading to delayed healing and perhaps other complications such as corneal infection and ulceration. The eyelid splint of the invention, however, is quite comfortable since it immobilizes the eyelid by gentle compression which is adjustable by the wearer. The invention works without the use of tape or flammable adhesives. The use of cotton pads and tape permits no capability of adjustment of corneal pressure by either the physician or the patient. With the present invention, the pressure can be initially set to be effective and comfortable; if the splint later becomes uncomfortable, the patient can reliably adjust it himself in the same manner, and reapply it. Because application of the splint is very simple, adult patients can be trusted to apply it themselves, whereas the current taped pads cannot be removed and reapplied by the patient.

Furthermore, the removability of the eyelid splint of the invention by the patient permits the patient to remove the patch intermittently if instructed by his physician for brief periods of physical and psychological relaxation, bathing, or to dry the face of rain or perspiration. In addition, it permits temporary use of the eye by the patient when absolutely necessary, for example, to drive a vehicle or for brief periods of essential work. In addition, it permits easy removal for application of medicine by the patient on a predetermined dosage schedule. If desired, the splint can be removed and reapplied without detaching the straps (i.e., simply stretching the straps and removing them over the top of the head), thereby ensuring that the original prescribed pressure on the eyelid will remain the same. This is very important in situations in which the splint must be removed by the patient, e.g., to drive home. After the pressure adjustment on the splint has been made by the physician, the device can be removed for a short period to assure a safe trip, and can easily be reapplied at the same pressure setting upon the patient's arrival at his destination.

The eyelid splint of the invention also has substantial advantage over the use of pads and tape in that it is much easier to apply, requiring less training of office and hospital staff, and can be applied in about one-fifth the time required to mount the pads and tape in place. Furthermore, pads cannot be successfully reapplied after removal. Indeed, taped pads often fall off due to improper applications or loss of adhesive due to perspiration.

It has been found that the use of the eyelid splint of the invention also causes substantially less patient anxiety during the wearing of the device, not only because the device is significantly more comfortable than prior art devices, but also because it can be removed for brief reprieves, thus rendering the device less confining both physically and emotionally.

A number of different head-encircling eye patches are known in the prior art. Examples of eye shields which are designed to cover the eye without contacting the eyelid or eyeball are Wylie, U.S. Pat. No. 591,244, Lush, U.S. Pat. No. 1,161,321, and Werner, U.S. Pat. No. 2,389,223. Various other types of eye bandages which may contain medicine-impregnated pads include Burdick, U.S. Pat. No. 915,738, Robinson, U.S. Pat. No. 1,642,661, Pedersen, U.S. Pat. No. 1,886,725, and Veysey, U.S. Pat. No. 2,024,491. A more complex eye shield which comprises an outer circular frame mounted over a transparent plastic bag filled with fluid to protect and moisten the eye is disclosed in Weiss, U.S. Pat. No. 4,473,370. None of the aforesaid devices have for their specific purpose immobilization of the eyelid, nor does their design provide for eyelid immobilization.

Accordingly, it is an object of the present invention to provide an eyelid splint for immobilizing a patient's eyelid which is comfortable to wear and which has an adjustable pressure to provide maximum comfort and therapeutic efficacy for the patient. It is another object of the invention to provide an eyelid splint which is inexpensive and easy to manufacture, and which is easy to temporarily remove and replace as necessary. These and other objects are achieved by the device of the information, a specific embodiment of which is described herein.

BRIEF SUMMARY OF THE INVENTION

An eyelid splint adapted to immobilize a patient's eyelid comprises a flexible resilient foam pad having a thickness of at least 10 mm, a backing on which the pad is mounted, and a pair of elastic straps extending from the backing for encircling the head of a patient and for mounting the pad in fixed position on the patient's eye. The straps each carry interengaging means near their ends, such as Velcro fasteners, for enabling the splint to be attached at various adjustable lengths.

BRIEF DESCRIPTION OF THE DRAWINGS

The invention is best understood with reference to the drawings, in which.

DETAILED DESCRIPTION OF A PREFERRED EMBODIMENT

Figure 1:
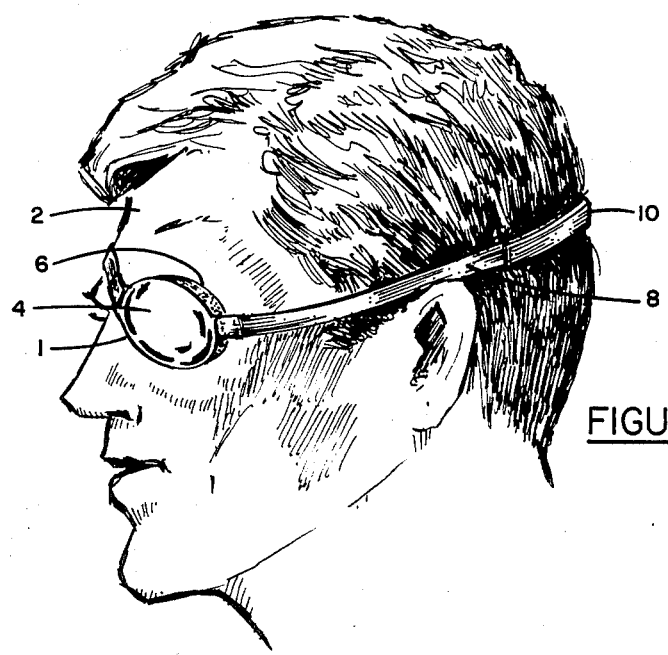
FIG. 1 is a perspective view showing a splint of the invention in place upon a patient.

Referring to FIG. 1, eyelid splint of the invention 1 is mounted on the eye of patient 2. The splint consists of a rigid backing member 4 having an elliptically shaped foam pad 6 mounted on the interior face thereof. A pair of head-encircling straps 8 and 10 extend from the backing member around the patient's head, and are fastened by patches of interengaging fastening means 12 and 14 carried near end portions of each strap.

Figure 2:
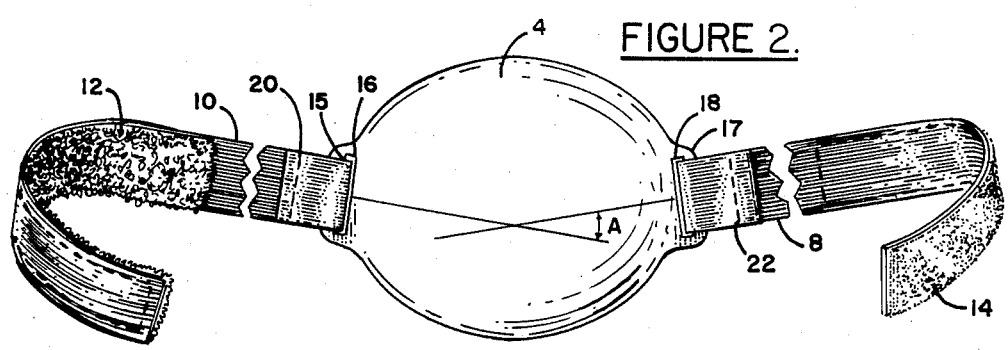
FIG. 2 is a front view of the splint.

A more detailed view of the splint of the invention is shown in FIG. 2. The straps, which are elastic, are mounted to the backing member by extending through rectangular slots 16 and 18 in lug portions 15 and 17 located at opposite sides of the backing member, and are attached by sewing as shown at stitching 20 and 22.

Figure 3:
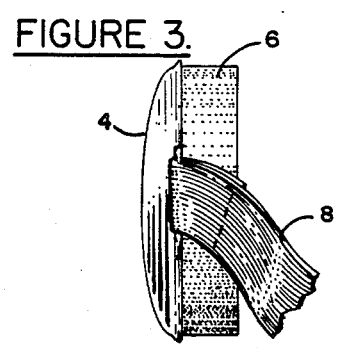
FIG. 3 is a side view of the splint.
Figure 4:
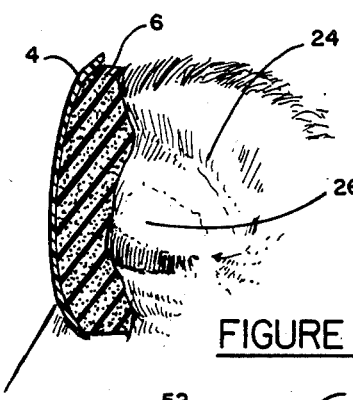
FIG. 4 is a partial side section view of the splint mounted on a patient's eye.
Figure 5:
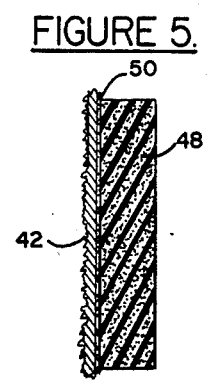
FIG. 5 is a partial side section view of an alternate embodiment of the splint.
Figure 6:
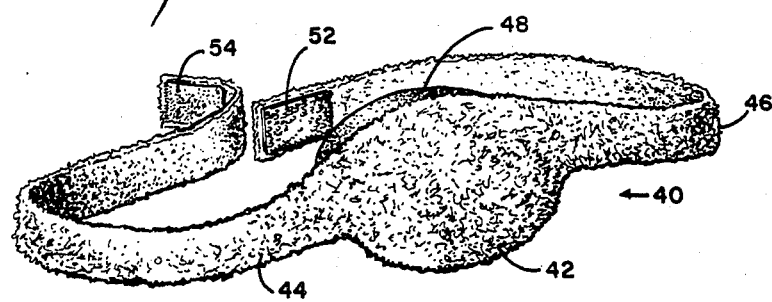
FIG. 6 is a perspective view of an alternate preferred embodiment of the splint of the invention.

The use of a solid backing for mounting the foam is optional; an alternate embodiment in which the straps and backing are fabricated from the same material is shown in FIGS. 5 and 6. However, when a solid backing member is used, the device may be typically dimensioned as follows. The device is oval in shape, having a height of about 45-50 mm and a distance between slot centers of 55-60 mm. The slots are straight and are angled outwardly from each other at a slight angle, with the angle "A" as shown in FIG. 2 being approximately equal to 20°. This permits the straps to extend in the proper directions around the patient's head. The slots are about 13 mm by 3 mm, and the strap has a width slightly less than the slot length. As seen in FIGS. 3 and 4, the rigid backing member is slightly concave on its interior surface, with a concavity of about 6 mm from the edge of the backing member to its center. The edge of the backing member extends outwardly around the edge of the foam pad by about 1 mm. If a rigid backing member is used, it may be fabricated from any generally rigid material, including metal, plastic, wood, cardboard, or similar material. The backing simply helps to compress the padded material against the eyelid in a uniform manner.

Whereas the shape, size, and material of the backing member are not particularly critical, the fabrication of pad 6 is extremely important. The compression pad may be made from a variety of synthetic foams, cotton, or any other synthetic soft material which is not a dermal irritant; the use of a highly resilient foam is substantially preferred. Any commercially available plastic foam, such as polyurethane, polyether, polystyrene, or polyethylene, may be used. A very important feature of the invention is that the foam be sufficiently thick and resilient as to enable the splint to be pressed against the eyelid firmly but without discomfort or risk of damage to the eye. In tests using an intercraneal pressure monitor, it has been found that the optimum amount of pressure exerted on the eyelid at its forwardmost point (i.e., maximum pressure exerted on the lid) should be no less than 23 mm Hg and no more than 40 mm Hg. Higher pressures may result in substantial discomfort and pain to the eye, whereas lower pressures do not enable proper splinting of the lid. In order to maintain the level of pressure within this relatively narrow region, the foam must be highly compressible. For example, when the unit is in place against the eyelid as is shown in FIG. 4, the pad contours comfortably to the interior portion of the orbital structure surrounding the eye. Therefore, pressure is applied at all points of the lid, preventing its movement. However, if the pressure on the lid at the forwardmost portion of the cornea exceeds 40 mm Hg, the splint will feel uncomfortable, and healing may be delayed or deterred. Accordingly, the thickness of the foam pad is extremely important to the efficacy of the apparatus of the invention. While the thickness will vary with the type and compressibility of the particular pad chosen, the thickness should be a minimum of 10 mm, and is preferably from about 12 to about 22 mm, more particularly 14–20 mm. The use of a thick foam enables a highly compressible foam to be chosen, thereby ensuring maximum patient comfort. A typical example of a preferred foam is one-pound density polyether foam having a compressibility of 5–20 psi, preferably 9–15 psi i.l.d. Denser, less compressible foams tend to result in less comfortable splints. Preferred foam density is 0.7–1.5 pounds/cu. ft., preferably about 1 pound. An example of acceptable foam is Scott M-105-12. The foam is attached to the rigid backing material by any known adhesive means. The pad is generally of uniform thickness, though it may be contoured slightly concave to fit the front contour of the eye if desired.

A variety of lightweight elastic straps can be used. Approximately 20 materials have been tested for their comfort, including softness of texture, breathability, weight and, most importantly, stretchability. The best materials were those composed of Spandex with one or more of nylon, polyester, and cotton.

Stretchability can be measured by Young's Modulus (YM). Since YM is a function of the cross-sectional area of the material, it can be compensated for by altering the width or thickness of the strap; however, straps less than 1.0 cm in width tend to be unstable on the head and those greater than 3.0 cm are less comfortable and cosmetically less desirable. Material thickness was generally not critical. The materials which provided a firm comfortable fit in the desirable width range were those whose YM fell between $2.0 \times 10^5$ and $2.0 \times 10^6$, which includes lightweight elastic bands and a few of the heavier elastic materials as used in girdles. An alternate measure is that a force of 1.75 newtons will stretch an acceptable material 5–50% of its length.

A particularly preferred embodiment of the invention is disclosed in FIGS. 5 and 6 of the drawings. In this embodiment, foam or sponge pad 48 is mounted on an elastic cloth backing 42 by means of adhesive 50. As shown in FIG. 6, the elastic backing 42 and elastic straps 44 and 46 are fabricated from an integral piece of the same material. Interengaging fastening means 50 and 52 are mounted on end portions of the elastic straps 44 and 46, respectively. It has been found that the elastic cloth backing 42 enables sufficient uniformity of pressure on the eyelid and is actually preferred to the version shown in FIGS. 1 and 2 due to increased comfort and safety. In addition, manufacturing simplicity is far superior, in that the backing and straps may be fabricated from a single piece of material. Preferred materials for the backing and straps of the version of the device of the invention shown in FIGS. 5 and 6 are the Spandex materials previously discussed.

Splints of the invention are designed to fit either eye of the patient. The splint is applied by holding the padded side against the closed eyelid, and, while the patient holds the padded backing against his closed eye, bringing the straps around to fasten across the occiput. The lateral strap passes across the user's temple and either across or just above the upper one-third of the ear; the medial strap passes above the contralateral eyebrow, across the forehead, and above the contralateral ear. The Velcro ends are then attached to secure the straps. If the splint feels too tight against the eye, it is loosened until comfortable by shortening the length of Velcro overlap. Once the patient reports a comfortable fit, he is told to blink both eyes rapidly and repeatedly, and is asked if the splinted eye is able to open. If it can open, the splint is tightened by increasing the overlap of the fasteners. If the patient later wishes to remove the splint by sliding it over his head, he may do so and replace it without altering the pressure adjustment. Alternatively, where the straps attach in the back, the interior strap can be marked with a pen at the distal edge of the exterior strap in case the patient inadvertently pulls the fastener apart. He can then reattach the Velcro ends at the mark under direct visualization and apply it by sliding it over his head to assure the same fit and pressure that was applied by the physician.

While any interengaging fastening means for attaching the straps may be used, such as snaps or buckles, Velcro fasteners are preferred because of the ease of attachment and adjustability. Velcro fasteners are well known in the fastening industry, and consist of opposing pairs of a large plurality of hooks and loops which interengage releasably when pressure is applied. Alternatively, a single strap may be used having both ends attached to the pad member or backing. In this embodiment, in order to avoid making a multiplicity of sizes of the splint, a relatively long strap is used, and adjustment is effected by using a conventional two-ring adjustment means, or by otherwise fastening (e.g. by stapling) portions of the strap loop together to shorten the strap to the desired length.

While the preferred thickness of the pad has been described as a minimum of 10 mm, a lower pad thickness (e.g., about 7 mm) may be used if the pad backing is redesigned. For example, if a convex shaped backing is used (as opposed to the concave backing shown in FIGS. 3 and 4), or if the elastic strap is attached to the backing by forwardly directed flanges on the backing (thus permitting the backing to be mounted closer to the eye socket while still maintaining the required pressure), a less thick pad may be used.

Having described several embodiments of the invention in detail, those skilled in the art will appreciate that numerous modifications may be made therein without departing from its spirit. Accordingly, the foregoing detailed description of these embodiments should not be considered limiting, and the invention should be considered defined only by the following claims.

I claim:

1. An eyelid splint adapted to immobilize an eyelid of only one eye of a patient consisting essentially of a flexible, resilient pad member adapted to press against the exterior of a patient's eyelid, said pad having a thickness of at least 14 mm, a backing member for mounting a pad thereon, and means for maintaining a pressure of 23–40 mm Hg on the eyelid, said means consisting essentially of an elastic strap means attached to the backing member for encircling the head of a patient, the strap means comprising first and second elastic strap members each having an end portion, and first and second interengaging fastening members comprising a plurality of mating hooks and loops mounted on the end portions of said straps for fastening said straps at adjustable lengths.

2. The splint of claim 1 wherein the pad is a foam pad having a thickness of from about 14 to about 22 mm.

3. The splint of claim 1 wherein the pad comprises a highly compressible foam pad having a density of from about 0.7–1.5 lbs/cu. ft.

4. An eyelid splint adapted to immobilize only one eyelid of a patient consisting essentially of
a flexible, resilient foam pad member having a thickness from about 12 to about 22 mm,
said foam pad having a compressibility of 5–20 psi i.l.d. and having a density from about 0.7–1.5 lbs/cu.ft.,
a backing member for mounting the pad thereon,
means for maintaining a pressure of 23–40 mm Hg on the eyelid, said means consisting essentially of
first and second elastic strap members attached respectively to opposite portions of said backing members at an angle of about 20° to each other, said straps being stretchable by a force of 1.75 newtons to 105%–150% of the unstretched length, and
Velcro fastening means mounted on said straps for fastening said straps at adjustable lengths.

5. The splint of claim 4 wherein the pad has a substantially uniform thickness.

6. The splint of claim 4 wherein the compressibility of the foam is from about 8 to about 15 psi i.l.d.

7. A method of immobilizing an eyelid of one eye only of a patient to permit healing of the cornea comprises applying to the eyelid an eyelid splint adapted to immobilize the eyelid, providing the splint with a flexible, resilient pad member adapted to press against the exterior of the patient's eyelid, said pad having a thickness of at least 14 mm and a backing member for mounting the pad thereon, maintaining a pressure on said eyelid of between 23–40 mm Hg, and providing means to maintain said pressure consisting of elastic strap means attached to the backing member for encircling the head of the patient and interengaging fastening means mounted on said elastic strap means to enable securing said strap means to the head of the patient at adjustable lengths.

8. The method of claim 7 wherein the pad is a foam pad having a thickness of from about 14 to about 22 mm and a density of 0.7–1.5 lbs/cu.ft.

* * * * *